(12) United States Patent
Beeckler et al.

(10) Patent No.: US 11,547,477 B2
(45) Date of Patent: Jan. 10, 2023

(54) HEAT TRANSFER THROUGH AN ABLATION ELECTRODE

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 141 days.

(21) Appl. No.: 16/696,713

(22) Filed: Nov. 26, 2019

(65) Prior Publication Data

US 2021/0153930 A1    May 27, 2021

(51) Int. Cl.
| | |
|---|---|
| *A61B 18/14* | (2006.01) |
| *A61B 90/00* | (2016.01) |
| *A61B 18/12* | (2006.01) |
| *A61B 17/00* | (2006.01) |
| *A61B 18/00* | (2006.01) |
| *A61M 25/01* | (2006.01) |
| *H01B 5/14* | (2006.01) |

(52) U.S. Cl.
CPC ...... *A61B 18/1492* (2013.01); *A61B 18/1206* (2013.01); *A61B 2017/00199* (2013.01); *A61B 2018/00077* (2013.01); *A61B 2018/00083* (2013.01); *A61B 2018/00166* (2013.01); *A61B 2018/00327* (2013.01); *A61B 2018/00351* (2013.01); *A61B 2018/00434* (2013.01); *A61B 2018/00577* (2013.01); *A61B 2018/00821* (2013.01); *A61B 2090/064* (2016.02); *A61B 2218/002* (2013.01); *A61B 2562/164* (2013.01); *A61B 2562/166* (2013.01); *A61M 25/0127* (2013.01); *H01B 5/14* (2013.01)

(58) Field of Classification Search
CPC ...... A61B 18/1492; A61B 2018/00077; A61B 2218/002; A61B 5/263; A61B 5/25; A61B 5/6852; A61N 1/06; A61N 1/0587
See application file for complete search history.

(56) References Cited

U.S. PATENT DOCUMENTS

| | | | |
|---|---|---|---|
| 6,241,724 B1 * | 6/2001 | Fleischman | ........ A61B 18/1492 600/374 |
| 8,456,182 B2 | 6/2013 | Bar-Tal et al. | |
| 2001/0021866 A1 | 9/2001 | Dobak et al. | |

(Continued)

OTHER PUBLICATIONS

Copending U.S. Appl. No. 15/990,532, filed May 25, 2018.
Copending U.S. Appl. No. 16/103,806, filed Aug. 14, 2018.

*Primary Examiner* — Jaymi E Della
(74) *Attorney, Agent, or Firm* — Frost Brown Todd LLC

(57) ABSTRACT

An apparatus includes a flexible electrically-insulating substrate including an inner surface and an outer surface. The substrate is shaped to define multiple channels passing between the inner surface and the outer surface, at least some of the channels being concave channels. The apparatus further includes an outer layer of an electrically-conducting metal covering at least part of the outer surface, an inner layer of the electrically-conducting metal covering at least part of the inner surface, and respective columns of the electrically-conducting metal that fill the channels such as to connect the outer layer to the inner layer.

18 Claims, 13 Drawing Sheets

(56) References Cited

U.S. PATENT DOCUMENTS

| | | |
|---|---|---|
| 2002/0045893 A1 | 4/2002 | Lane et al. |
| 2005/0004440 A1* | 1/2005 | Vanney .............. A61B 18/1492 |
| | | 600/374 |
| 2007/0219551 A1 | 9/2007 | Honour et al. |
| 2014/0058386 A1* | 2/2014 | Clark .................... A61B 18/14 |
| | | 606/41 |
| 2014/0073853 A1 | 3/2014 | Swisher et al. |
| 2014/0276758 A1 | 9/2014 | Lawrence et al. |
| 2015/0272669 A1 | 10/2015 | Brucker et al. |
| 2015/0351652 A1* | 12/2015 | Marecki ............. A61B 18/1492 |
| | | 600/374 |
| 2017/0143414 A1* | 5/2017 | Sliwa ................. A61B 18/1492 |
| 2018/0110562 A1* | 4/2018 | Govari ............... A61B 18/1492 |

* cited by examiner

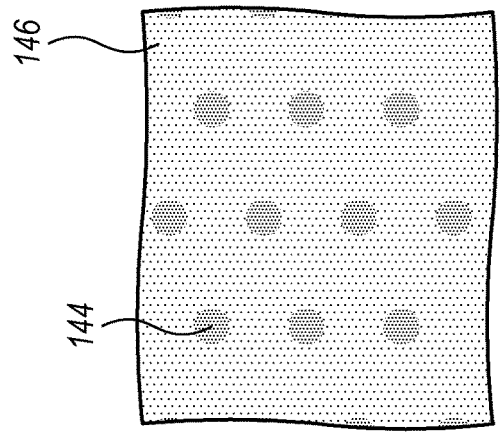
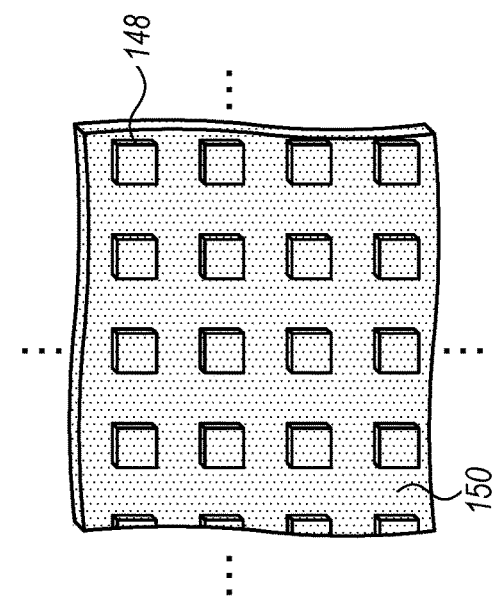
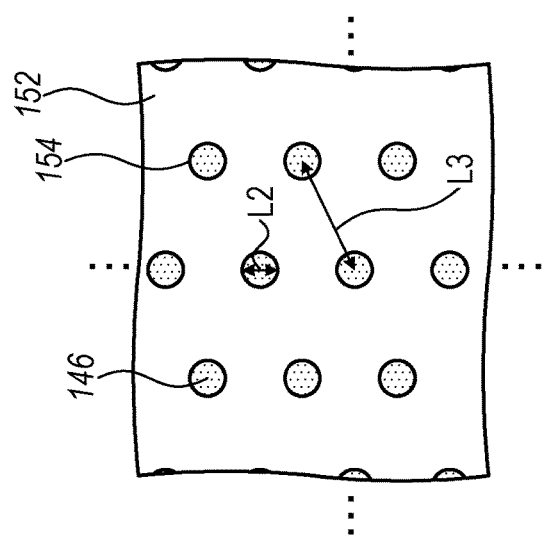
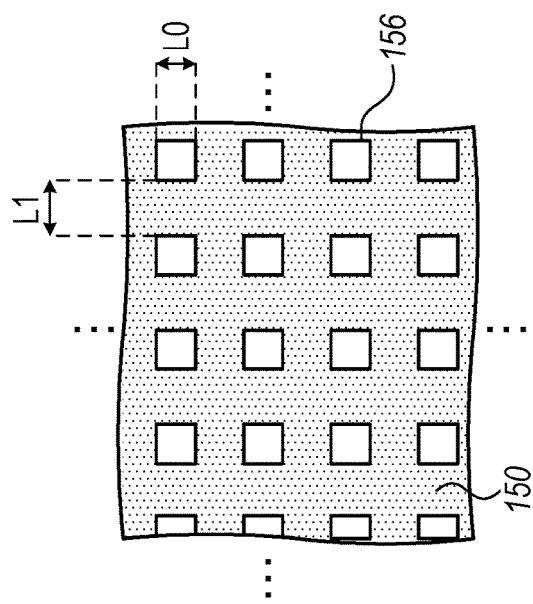
FIG. 6A
FIG. 6B

HEAT TRANSFER THROUGH AN ABLATION ELECTRODE

FIELD OF THE INVENTION

The present invention is related to intrabody probes and the use thereof in ablation procedures.

BACKGROUND

In some ablation procedures, an electrode disposed at the distal end of an intrabody probe is brought into contact with tissue, and radiofrequency (RF) energy is then passed from the electrode into the tissue.

US Patent Application Publication 2018/0110562, issued as U.S. Pat. No. 10,898,262 on Jan. 26, 2021, whose disclosure is incorporated herein by reference, describes a catheter that includes an insertion tube, a flexible substrate, and one or more electrical devices. The insertion tube is configured for insertion into a patient body. The flexible substrate is configured to wrap around a distal end of the insertion tube and includes electrical interconnections. The electrical devices are coupled to the flexible substrate and are connected to the electrical interconnections.

SUMMARY OF THE INVENTION

There is provided, in accordance with some embodiments of the present invention, an apparatus including a flexible electrically-insulating substrate. The substrate includes an inner surface and an outer surface and is shaped to define multiple channels passing between the inner surface and the outer surface, at least some of the channels being concave channels. The apparatus further includes an outer layer of an electrically-conducting metal covering at least part of the outer surface, an inner layer of the electrically-conducting metal covering at least part of the inner surface, and respective columns of the electrically-conducting metal that fill the channels such as to connect the outer layer to the inner layer.

In some embodiments, each of the concave channels includes:
a circular central channel-portion; and
one or more peripheral channel-portions having arced perimeters and opening into the central channel-portion.

In some embodiments, the peripheral channel-portions consist of between two and eight peripheral channel-portions.

In some embodiments, the peripheral channel-portions consist of six peripheral channel-portions.

In some embodiments, some of the channels are circular channels, and the channels are arranged such that each of at least some of the circular channels is surrounded by a respective three of the concave channels.

In some embodiments, each of the concave channels includes:
a polygonal central channel-portion; and
one or more peripheral channel-portions opening into the central channel-portion.

In some embodiments, the central channel-portion and peripheral channel-portions are rectangular.

In some embodiments, each of the concave channels has a star shape.

In some embodiments, a total area of respective outer openings of the channels is at least 30% of an area of the outer surface.

In some embodiments, the electrically-conducting metal includes gold.

In some embodiments, the apparatus further includes:
a probe configured for insertion into a body of a subject; and
a supporting structure bonded to the inner layer and coupled to a distal end of the probe.

In some embodiments, the supporting structure includes a plurality of ribs surrounding a lumen, successive ones of the ribs being separated from one another by an aperture that is wider than each of the ribs.

In some embodiments, a surface of the inner layer is shaped to define a plurality of depressions.

In some embodiments, the depressions are circular and are arranged in a close-packed pattern.

In some embodiments, an average transverse cross-sectional area of each of the concave channels is between 345 and 15,700 $\mu m^2$.

There is further provided, in accordance with some embodiments of the present invention, a method including inserting, into a body of a subject, a distal end of a probe that includes a substrate having an inner surface, which is covered at least partly by an inner metallic layer, and an outer surface, which is covered at least partly by an outer metallic layer, the substrate being shaped to define multiple channels, which pass between the inner surface and the outer surface and are filled by metal columns, at least some of the channels being concave channels. The method further includes, subsequently to inserting the distal end of the probe into the body of the subject, contacting tissue of the subject with the outer metallic layer. The method further includes, while contacting the tissue, passing an electric current, via the outer metallic layer, into the tissue, such that heat is generated in the tissue and is transferred, via the metal columns, to the inner metallic layer. The method further includes evacuating the heat, from the inner metallic layer, into blood of the subject, by passing an irrigating fluid through the substrate.

In some embodiments, the tissue includes cardiac tissue of the subject.

There is further provided, in accordance with some embodiments of the present invention, a method including forming multiple channels, at least some of which are concave channels, in a flexible electrically-insulating substrate, such that the channels pass between an inner surface of the substrate and an outer surface of the substrate. The method further includes, using an electrically-conducting metal, at least partly covering the inner surface and the outer surface and filling the channels.

In some embodiments, forming the channels includes:
forming a close-packed pattern of circular channels; and
subsequently to forming the close-packed pattern, forming the concave channels by expanding some of the circular channels such that each of the expanded circular channels opens into a surrounding six of the circular channels.

In some embodiments, the method further includes:
bonding the electrically-conducting metal that covers the inner surface to a supporting structure; and
coupling the supporting structure to a distal end of a probe configured for insertion into a body of a subject.

In some embodiments, the method further includes forming a plurality of depressions in a surface of the inner layer.

In some embodiments, forming the depressions includes forming circular depressions in a close-packed pattern.

The present invention will be more fully understood from the following detailed description of embodiments thereof, taken together with the drawings, in which:

BRIEF DESCRIPTION OF THE DRAWINGS

FIG. 6A is a schematic illustration of a method for forming depressions in a surface of a supporting structure, in accordance with some embodiments of the present invention;

FIG. 6B is a schematic illustration of a method for forming protrusions on a surface of a supporting structure, in accordance with some embodiments of the present invention;

DETAILED DESCRIPTION OF EMBODIMENTS

Glossary

Figure 1:
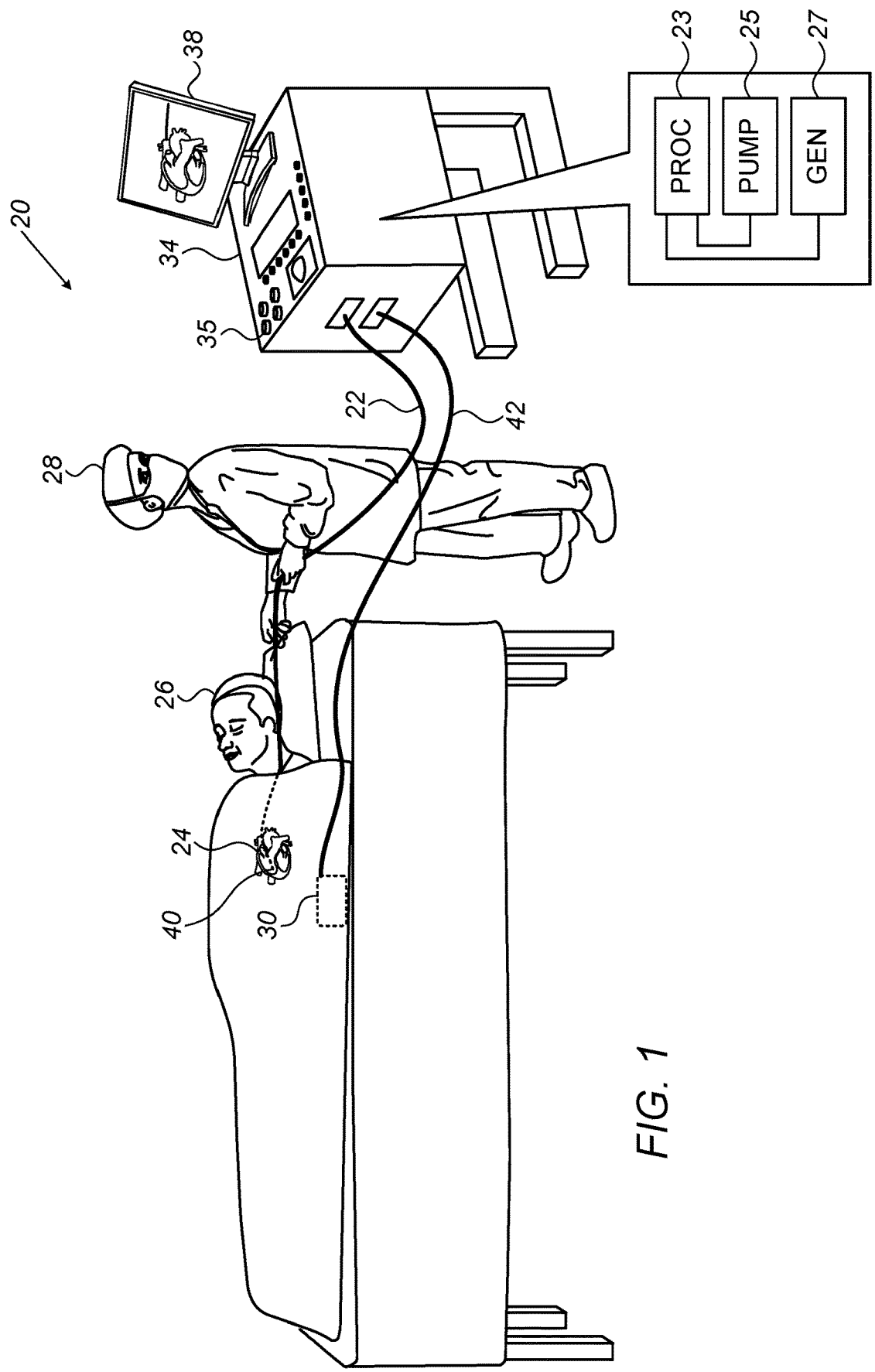
FIG. 1 is a schematic illustration of a system for ablating tissue of a subject, in accordance with some embodiments of the present invention.

A concave perimeter protrudes inward, such that a line joining two points within the perimeter at opposite sides of the protrusion passes outside the perimeter. In contrast, any line joining two points within a convex (or "non-concave") perimeter does not pass outside the perimeter.

In the context of the present application, including the claims, the "perimeter" of a channel or via generally refers to the perimeter of the transverse cross-section of the channel or via. Similarly, unless indicated otherwise, the "shape" of a channel or via generally refers to the shape of the perimeter of the channel or via.

In the context of the present application, including the claims, a concave channel or via is a channel or via having a concave perimeter. Conversely, a convex channel or via is any channel or via having a convex perimeter. (In general, a channel or via that is slightly concave due to imperfections in the manufacturing techniques used to form the channel or via is considered herein to be convex, rather than concave.)

Overview

Embodiments of the present invention include an ablation electrode comprising at least one flexible printed circuit board (PCB) that is bonded, by an adhesive, to a supporting structure. The flexible PCB comprises a flexible electrically-insulating substrate comprising an outer surface that is coated by an outer layer of an electrically-conducting and biocompatible metal, such as gold, palladium, or platinum, and an inner surface that is coated by an inner layer of the same and/or another electrically-conducting metal. As further described below, the metal may be deposited onto the substrate by placing the substrate into a plating bath for a period of time.

The inner surface may further support one or more electric components such as sensors (e.g., thermocouples) and traces, which are electrically isolated from the inner metallic layer. Following the deposition of these electric components and the coating of the substrate, the PCB is bonded to the supporting structure. Subsequently to or concurrently with the bonding, the flexible PCB may be deformed into any suitable shape. For example, in some embodiments, the flexible PCB is deformed into a thimble-shaped electrode, referred to hereinbelow as a "tip electrode." The electrode is then coupled to the distal end of an intrabody probe.

During an ablation procedure, the outer metallic layer is brought into contact with the tissue that is to be ablated, and ablating currents are then passed, via the outer metallic layer, into the tissue. While the ablating currents are applied to the tissue, the sensors may acquire any relevant physiological readings from the tissue. Typically, plated vias, which pass through the electrode, provide electrical connectivity between the inner and outer metallic layers, such that the ablating currents may pass outward through the plated vias, and electrographic signals from the tissue may pass inward through the plated vias. Electrical connectivity may also be provided by blind vias, each such via being formed by the removal of a portion of the substrate, such that the outer metallic layer directly contacts a trace underneath.

The aforementioned plated vias also provide fluid communication between the inner and outer surfaces of the electrode, such that an irrigating fluid (e.g., saline) may pass through the plated vias into the surrounding blood. The irrigating fluid evacuates heat from the interior of the electrode into the blood, and additionally dilutes the blood at the tissue-electrode interface, thus reducing the probability of coagulum or charring. Due to the fact that the plated vias provide for passage of the irrigating fluid therethrough, the plated vias may also be referred to as "irrigation channels" or "irrigation holes."

A challenge, when using the type of electrode described above, is that the substrate may provide significant thermal resistance, such as to limit the amount of heat that is transferred from the tissue-electrode interface to the interior of the electrode. This, in turn, limits the amount of heat that may be evacuated by the irrigating fluid.

U.S. application Ser. Nos. 15/990,532, published as U.S. Pub. No. 2019/0357972 on Nov. 28, 2019, and 16/103,806, published as U.S. Pub. No. 2020/0054390 on Feb. 20, 2020, the respective disclosures of which are incorporated herein by reference, address this challenge by providing closed vias, referred to hereinbelow as "thermal vias," that increase the thermal conductivity between the two surfaces of the electrode. Such thermal vias may comprise, for example, columns of gold that fill channels drilled through the substrate and thus connect the outer metallic layer to the inner metallic layer. The thermal vias increase the amount of heat that is transferred to the interior of the electrode, thus facilitating the evacuation of heat by the irrigating fluid.

In general, the degree of thermal conductivity provided by the thermal vias is a function of the total cross-sectional area of the metal that fills the thermal vias. However, as the inventors have discovered, attaining a sufficient total cross-sectional area may be difficult using thermal vias having a convex cross-sectional profile, such as a circular cross-sectional profile. In particular, if the cross-sectional area of any one of the thermal vias is too large, it may take a relatively long time for the via to be filled during the plating process, such that, while the via is being filled, the layer of metal covering the surface of the substrate may become too thick. Hypothetically, a large number of smaller thermal vias may be provided; however, this may require placing the vias too close together, thus compromising the structural integrity of the substrate.

Embodiments of the present invention therefore provide concave thermal vias, in which the perimeter of the via protrudes into the via. The protrusions provide additional area onto which the metal may nucleate during the plating process, and also decrease the distance from the perimeter to the interior of the via, thus expediting the filling of the vias. Hence, each concave thermal via may have a relatively large cross-sectional area without unduly increasing the duration of the plating process. In some embodiments, the concave thermal vias are interspersed with smaller, convex thermal vias.

Alternatively or additionally, various other techniques may be used to facilitate the transfer of heat to the irrigating fluid, as described in detail below. For example, the supporting structure may be shaped to define large apertures that expose the inner metallic layer to the irrigating fluid. In addition, the inner metallic layer may be shaped to define multiple depressions that increase the turbulence of the flow of the fluid over the inner metallic layer.

System Description

Reference is initially made to FIG. 1, which is a schematic illustration of a system 20 for ablating tissue of a subject 26, in accordance with some embodiments of the present invention.

FIG. 1 depicts a physician 28 performing an ablation procedure on subject 26, using an intrabody probe 22. In this procedure, physician 28 first inserts an ablation electrode 40, disposed at the distal end of probe 22, into the subject, and then navigates electrode 40 to the tissue that is to be ablated. For example, the physician may advance the electrode through the vasculature of the subject until the electrode is in contact with cardiac tissue belonging to the heart 24 of the subject. Next, while electrode 40 contacts the tissue, the physician causes radiofrequency (RF) electric currents to be passed between the ablation electrode and another electrode, such that the electric currents generate heat in the tissue. For example, in a unipolar ablation procedure, the electric currents may be passed between the ablation electrode and a neutral electrode patch 30 that is coupled externally to the subject, e.g., to the subject's back.

To facilitate navigating probe 22, the probe may comprise one or more electromagnetic position sensors, which, in the presence of an external magnetic field, generate signals that vary with the positions of the sensors. Alternatively or additionally, any other suitable tracking system, such as an impedance-based tracking system, may be used. For example, both electromagnetic tracking and impedance-based tracking may be used, as described, for example, in U.S. Pat. No. 8,456,182, whose disclosure is incorporated herein by reference.

Probe 22 is proximally connected to a console 34, comprising, for example, a processor (PROC) 23, a pump 25, and a signal generator (GEN) 27. (Electrode patch 30 is typically also connected to console 34, via a cable 42.) During the ablation procedure, signal generator 27 generates the aforementioned ablating currents. These currents are carried through probe 22, over one or more wires, to electrode 40. Additionally, pump 25 supplies an irrigating fluid, such as saline, to the distal end of the probe, as further described below with reference to FIGS. 2A-B and FIG. 3C.

Console 34 further comprises controls 35, which may be used by the physician to control the parameters of the ablating currents. In particular, in response to the manipulation of controls 35 by physician 28, processor 23 may adjust the parameters of the ablating currents, by outputting appropriate instructions to signal generator 27 over any suitable wired or wireless communication interface. Processor 23 may similarly control pump 25 over any suitable wired or wireless interface. In addition, the processor may receive and process any relevant signals from the distal end of the probe, such as the signals received from any of the sensors described herein.

In some embodiments, system 20 further comprises a display 38, which may display relevant output to physician 28 during the procedure.

Notwithstanding the particular type of procedure depicted in FIG. 1, it is noted that the embodiments described herein may be applied to any other suitable type of ablation procedure, such as an otolaryngological or a neurological ablation procedure, or any other procedure that necessitates the transfer of heat through a flexible PCB, such as the evacuation of heat from a circuit board into a surrounding fluid.

The Ablation Electrode

Figure 2A:
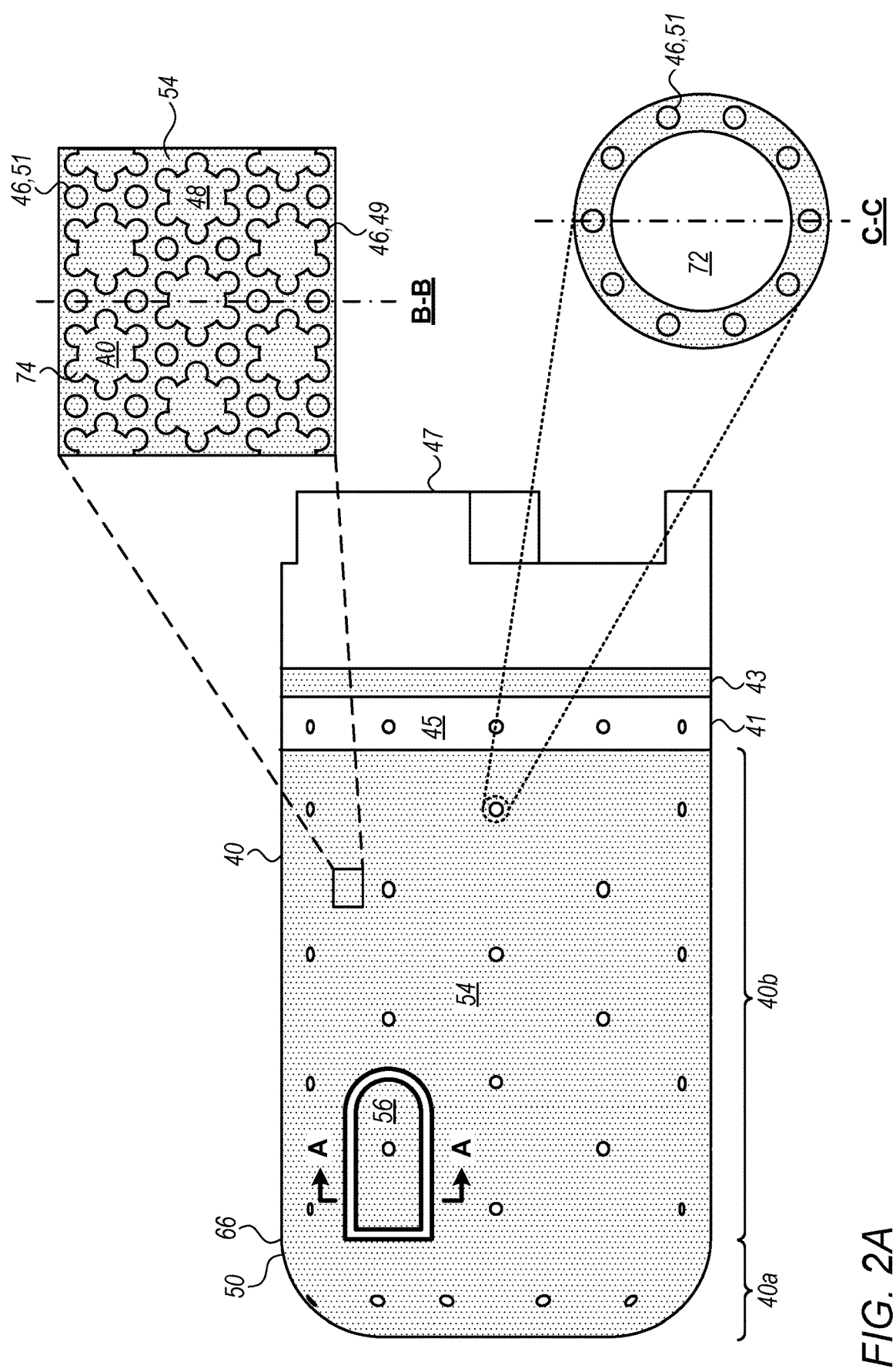
FIG. 2A is a schematic illustration of an ablation electrode, in accordance with some embodiments of the present invention.
Figure 2B:
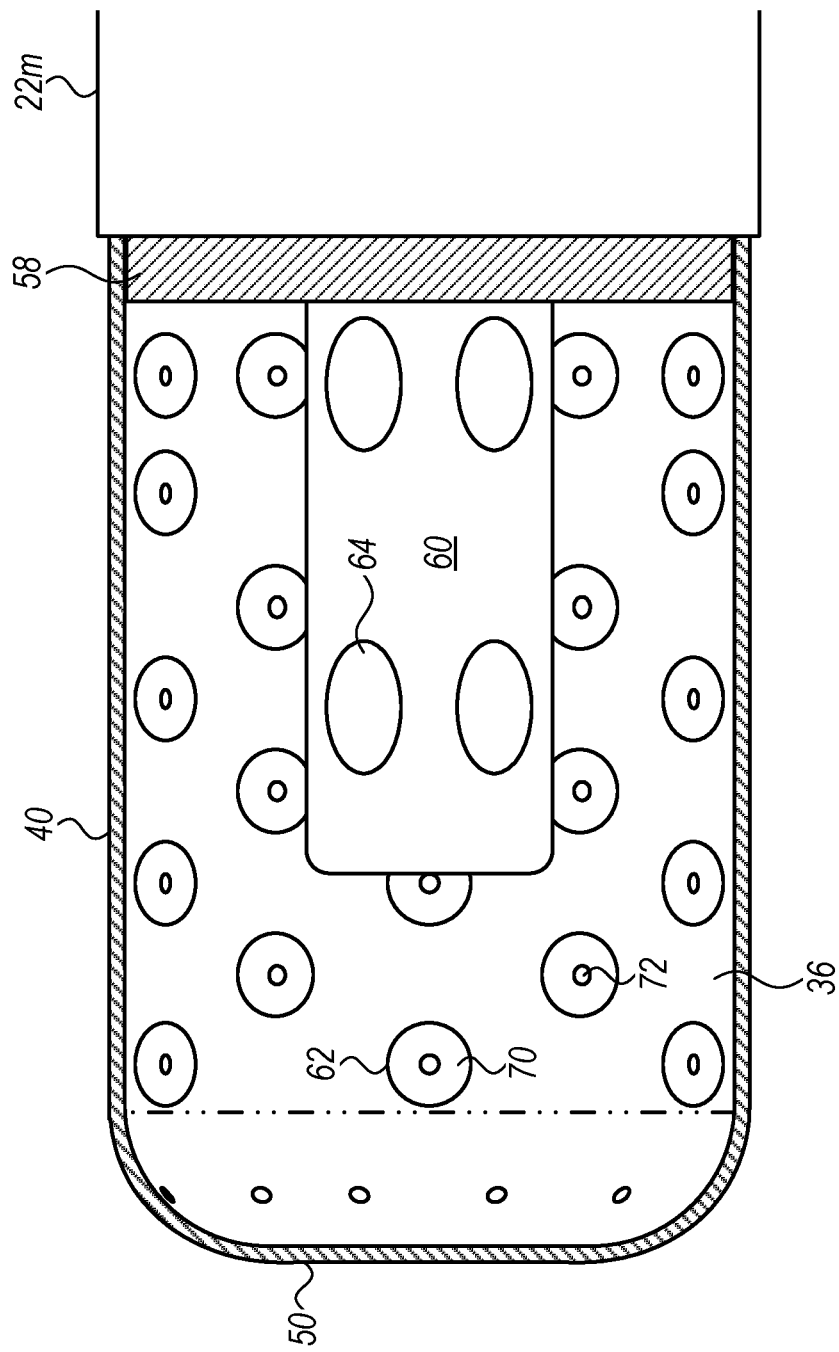
FIG. 2B schematically illustrates a longitudinal cross-section through the ablation electrode shown in FIG. 2A, in accordance with some embodiments of the present invention.

Reference is now made to FIG. 2A, which is a schematic illustration of ablation electrode 40, in accordance with some embodiments of the present invention. Reference is additionally made to FIG. 2B, which schematically illustrates a longitudinal cross-section through electrode 40, in accordance with some embodiments of the present invention.

As described above with reference to FIG. 1, probe 22 comprises at least one ablation electrode 40, such as the tip electrode depicted in FIGS. 2A-B. Electrode 40 comprises a plated flexible electrically-insulating substrate 41 that is bonded, by an adhesive, to a supporting structure 36 at the distal end of probe 22. Substrate 41 may be made of any suitable flexible electrically-insulating material, such as a flexible polymer (e.g., polyimide) or liquid crystal polymer (LCP). Supporting structure 36 may be made of any suitably strong material, such as cobalt chromium, stainless steel, magnesium, or a polymer. For example, the supporting structure may comprise an alloy of cobalt chromium, such as the L-605 cobalt-chromium-tungsten-nickel alloy, or polyether ether ketone (PEEK), such as glass-filled PEEK.

In general, electrode 40 may have any suitable shape. In some embodiments, as shown in FIGS. 2A-B, electrode 40 is thimble-shaped, comprising a cylindrical portion 40b capped by a dome-shaped portion 40a. Typically, tabs 47 at the proximal end of the electrode comprise soldering pads onto which wires, which run through the length of the probe, may be soldered, such as to establish electrical connectivity between the electrode and the proximal end of the probe. These soldering pads are described in further detail below with reference to FIGS. 4-5.

Figure 3A:
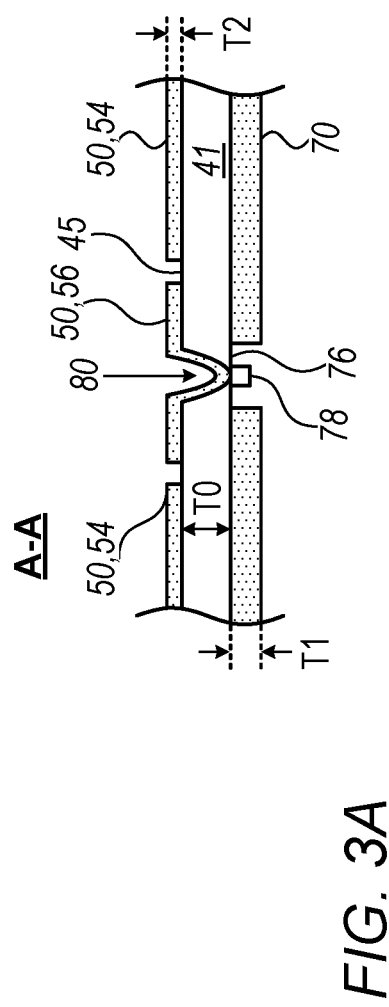
FIG. 3A is a schematic illustration of a cross-section through the surface of the ablation electrode shown in FIG. 2A, in accordance with some embodiments of the present invention.

Reference is now additionally made to FIG. 3A, which is a schematic illustration of a cross-section through the surface of electrode 40, in accordance with some embodiments of the present invention. FIG. 3A corresponds to the "A-A" cross-section indicated in FIG. 2A.

Substrate 41 comprises an inner surface 76, which faces supporting structure 36, and an outer surface 45, which faces away from supporting structure 36. Typically, the thickness T0 of the substrate—i.e., the distance between the inner and outer surfaces of the substrate—is between 5 and 75 (e.g., between 12 and 50) microns. At least part of the inner surface is covered by an inner layer 70 of an electrically-conducting metal, such as gold. Typically, inner layer 70 has a thickness T1 of between 10 and 50 microns. Similarly, at least part of outer surface 45 is covered by an outer layer 50 of the metal. Typically, outer layer 50 has a thickness T2 of between 1 and 50 microns, e.g., 5-35 microns.

Typically, outer layer 50 is discontinuous, in that the outer layer comprises a main portion 54 along with one or more isolated portions that are electrically isolated from main portion 54 by exposed portions of the substrate. These isolated portions may include one or more "islands" that function as sensing microelectrodes 56. For example, outer layer 50 may comprise 3-7 microelectrodes 56 distributed around the circumference of the electrode. Alternatively or additionally, the isolated portions may comprise a sensing ring electrode 43, which may be disposed, for example, near the proximal end of electrode 40.

A respective electrically-conductive trace 78, which is electrically isolated from inner layer 70 by an exposed portion of inner surface 76, is disposed beneath each of the sensing electrodes. As further described below with reference to FIG. 4, prior to forming the sensing electrodes, holes, referred to herein as blind vias 80, are formed (e.g., drilled) in the substrate above traces 78. Subsequently, as the sensing electrodes are deposited onto the outer surface of the substrate, the sensing electrodes at least partly fill blind vias 80, thus contacting the traces. Hence, during the procedure, electrographic signals from the cardiac tissue of the subject that are sensed by the sensing electrodes may be carried over traces 78 to wires that run through probe 22 to the proximal end of the probe. The signals may thus be delivered to processor 23 (FIG. 1) for analysis.

Figure 3B:
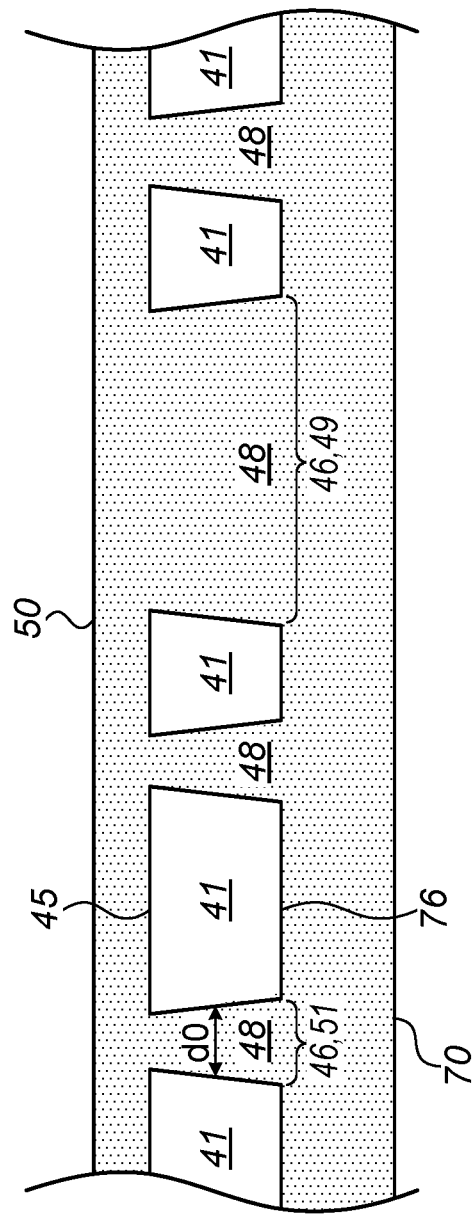
FIG. 3B is a schematic illustration of thermal vias passing through the surface of the ablation electrode shown in FIG. 2A, in accordance with some embodiments of the present invention.

Reference is now additionally made to FIG. 3B, which is a schematic illustration of thermal vias passing through the surface of electrode 40, in accordance with some embodiments of the present invention. FIG. 3B corresponds to the "B-B" cross-section indicated in FIG. 2A.

Substrate 41 is shaped to define multiple channels 46 passing between inner surface 76 and outer surface 45 of the substrate. Typically, each channel 46 is tapered along the length of the channel, in that the transverse cross-sectional area of the channel at the inner surface of the substrate is slightly greater than the transverse cross-sectional area at the outer surface.

As can be observed in FIG. 2A, at least some of channels 46 are concave channels 49, described in further detail below with reference to FIGS. 9-10. Optionally, the channels may further include one or more convex channels 51. In some embodiments, each convex channel 51 is circular, having a diameter d0 of between 5 and 50 (e.g., between 5 and 30) microns.

As described above in the Overview, by virtue of the concavity of channels 49, the transverse cross-sectional area A0 of each channel 49 may be relatively large. For example, the average transverse cross-sectional area of each of the concave channels may be between 345 and 15,700 pmt. Alternatively or additionally, the total area of the respective outer openings of channels 46—including the concave channels and any convex channels—may be at least 30% of the area of the outer surface.

Channels 46 are filled by respective columns 48 of the electrically-conducting metal, which connect outer layer 50 to inner layer 70. Columns 48 may have any suitable three-dimensional shape, this shape depending on the three-dimensional shape of channels 46. By virtue of the heat conducted by columns 48, the filled channels 46 are referred to herein as thermal vias 74. (For simplicity, no thermal vias are shown in FIG. 3A, which was described above.)

Figure 3C:
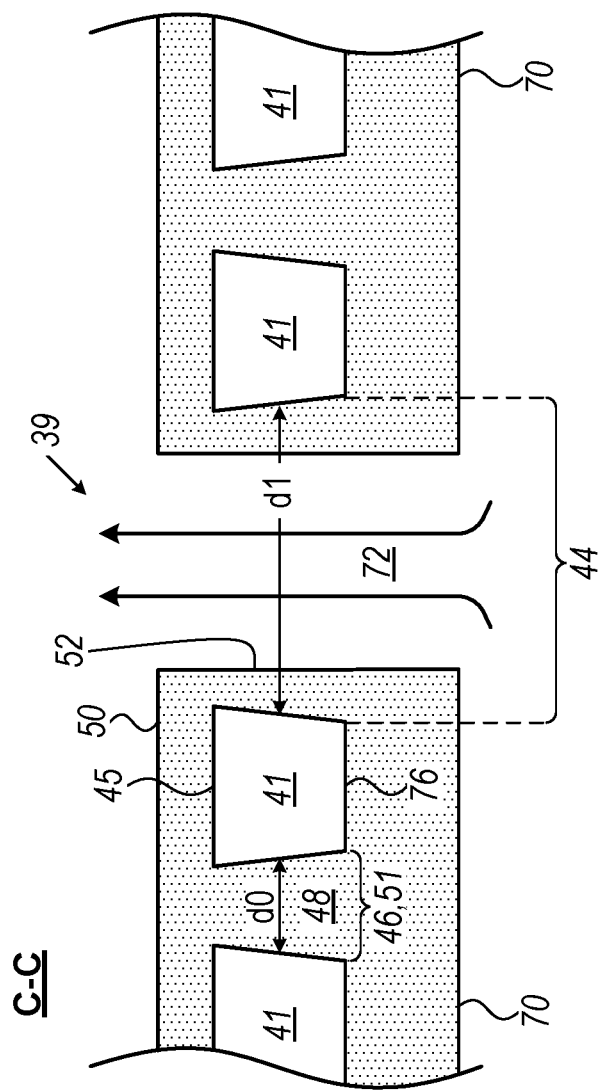
FIG. 3C is a schematic illustration of an irrigation hole passing through the surface of the ablation electrode shown in FIG. 2A, in accordance with some embodiments of the present invention.

Reference is now additionally made to FIG. 3C, which is a schematic illustration of an irrigation hole 72 passing through the surface of electrode 40, in accordance with some embodiments of the present invention. FIG. 3C corresponds to the "C-C" cross-section indicated in FIG. 2A.

Typically, substrate 41 is further shaped to define a plurality of wider channels 44, each wider channel 44 being plated by a plating layer 52 of the electrically-conducting metal that connects outer layer 50 to inner layer 70. Typically, each wider channel 44 is circular, having a diameter d1 of between 50 and 300 microns. Channels 44 are referred to herein as "wider" channels due to the fact that the transverse cross-sectional area of each channel 44 is typically greater than that of each channel 46. For the same reason, channels 46 are referred to hereinbelow as "narrower channels."

Typically, the electrode includes 30-100 wider channels. The plated wider channels provide electrical and thermal conductivity between the outer and inner layers of metal. Moreover, the plated wider channels provide a fluid passageway between the interior and exterior of the electrode, such that an irrigating fluid 39, supplied by pump 25 (FIG. 1), may flow therethrough. Hence, the plated wider channels are referred to herein as "irrigation holes" 72. (The diameter of each irrigation hole is smaller than diameter d1 by approximately twice the thickness of plating layer 52.)

As can be seen in FIG. 2B, supporting structure 36 is shaped to define apertures 62 that are aligned with irrigation holes 72, such that the supporting structure does not obstruct the irrigation holes. In some embodiments, as further described below with reference to FIG. 8, apertures 62 also expose a relatively large area of inner layer 70, thus increasing the transfer of heat to the irrigating fluid by exposing the inner layer to the fluid.

Typically, probe 22 comprises a fluid-delivery tube (not shown), which runs through the full length of the tubular body 22m of probe 22. The fluid-delivery tube is distally coupled to a flow diverter 60 that is shaped to define one or more fluid-flow apertures 64. Flow diverter 60 diverts fluid 39, which is received, via the fluid-delivery tube, from the proximal end of the probe, through fluid-flow apertures 64. In such embodiments, electrode 40 may be coupled to the base 58 of flow diverter 60, such that the flow diverter is disposed inside of the interior lumen of the electrode. For example, supporting structure 36 may be bonded to base 58. Alternatively or additionally, base 58 may be shaped to define a plurality of protrusions, and supporting structure 36 may be shaped to define a plurality of complementary holes, such that the protrusions snap into the holes.

As described above with reference to FIG. 1, during the ablation procedure, physician 28 contacts tissue of subject 26 with electrode 40, and in particular, with outer layer 50. While contacting the tissue with outer layer 50, the physician passes electric currents, via the outer layer, into the tissue. The electric currents cause heat to be generated in the tissue, such that a lesion is formed in the tissue. This heat is transferred, via thermal vias 74 (i.e., via columns 48) to inner layer 70. At the same time, pump 25 (FIG. 1) pumps irrigating fluid 39 through the fluid-delivery tube, such that the fluid flows into the interior of the electrode through fluid-flow apertures 64 of flow diverter 60. This fluid then flows out of the electrode through apertures 62 and irrigation holes 72, thus evacuating the heat from inner layer 70 into the subject's blood.

It is noted that outer layer 50, inner layer 70, plating layer 52 and columns 48 may be collectively described as a single body of metal that covers the substrate. It is further noted that in some embodiments, narrower channels 46 are not filled, but rather, are merely plated, similarly to wider channels 44. Even in such embodiments, however, a large amount of heat may be transferred to the interior of the electrode.

Manufacturing the Ablation Electrode

Figure 4:
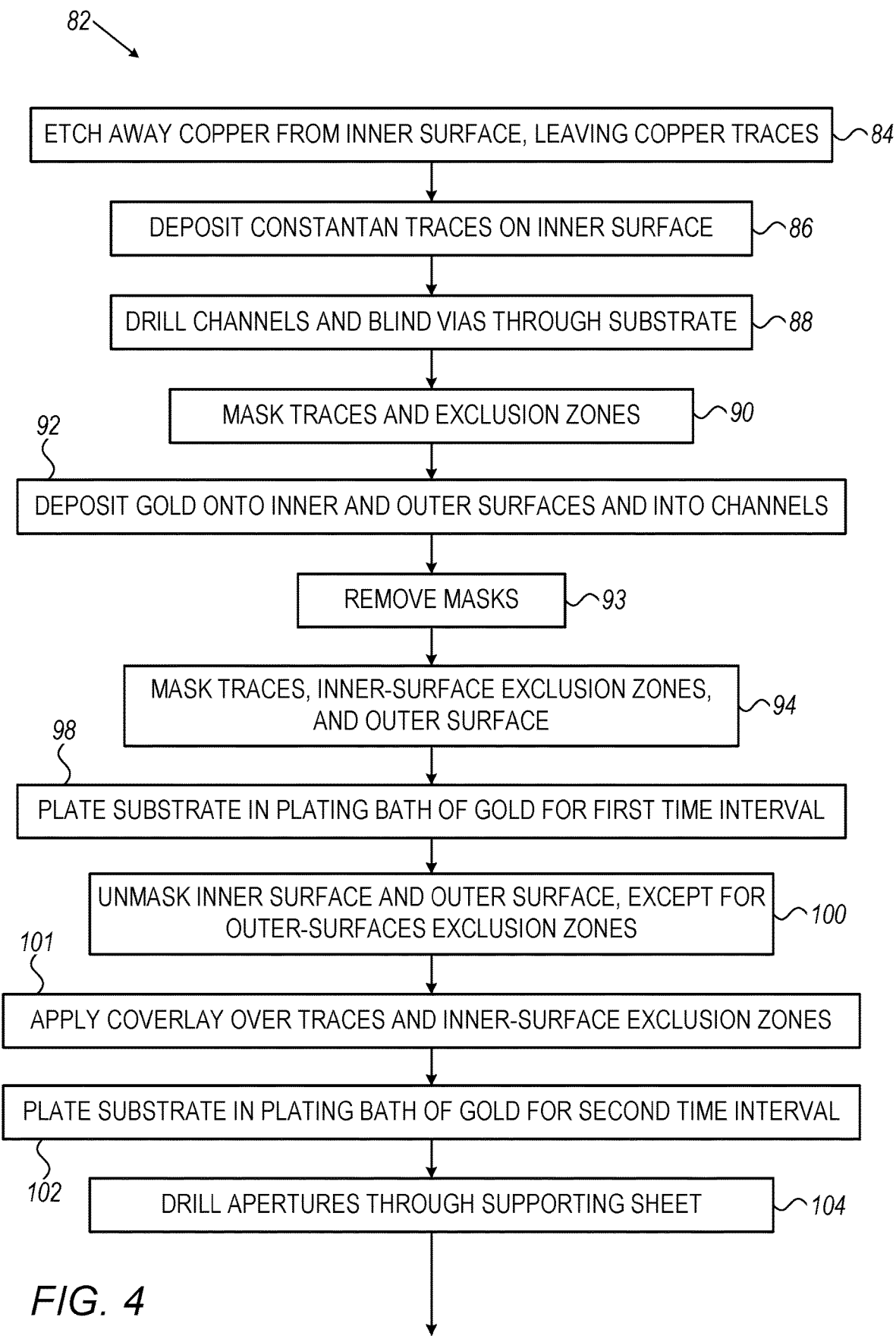
FIG. 4 is a flow diagram for a method of manufacturing an ablation electrode, in accordance with some embodiments of the present invention.
Figure 4:
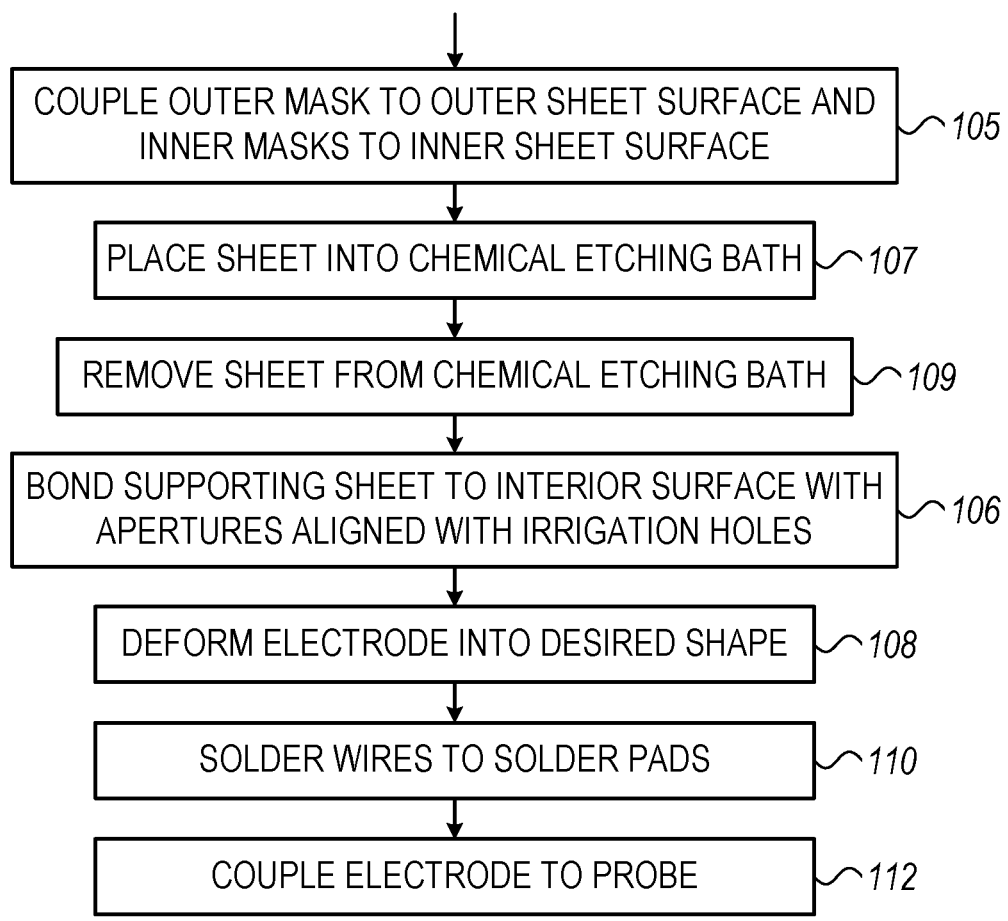
Figure 5:
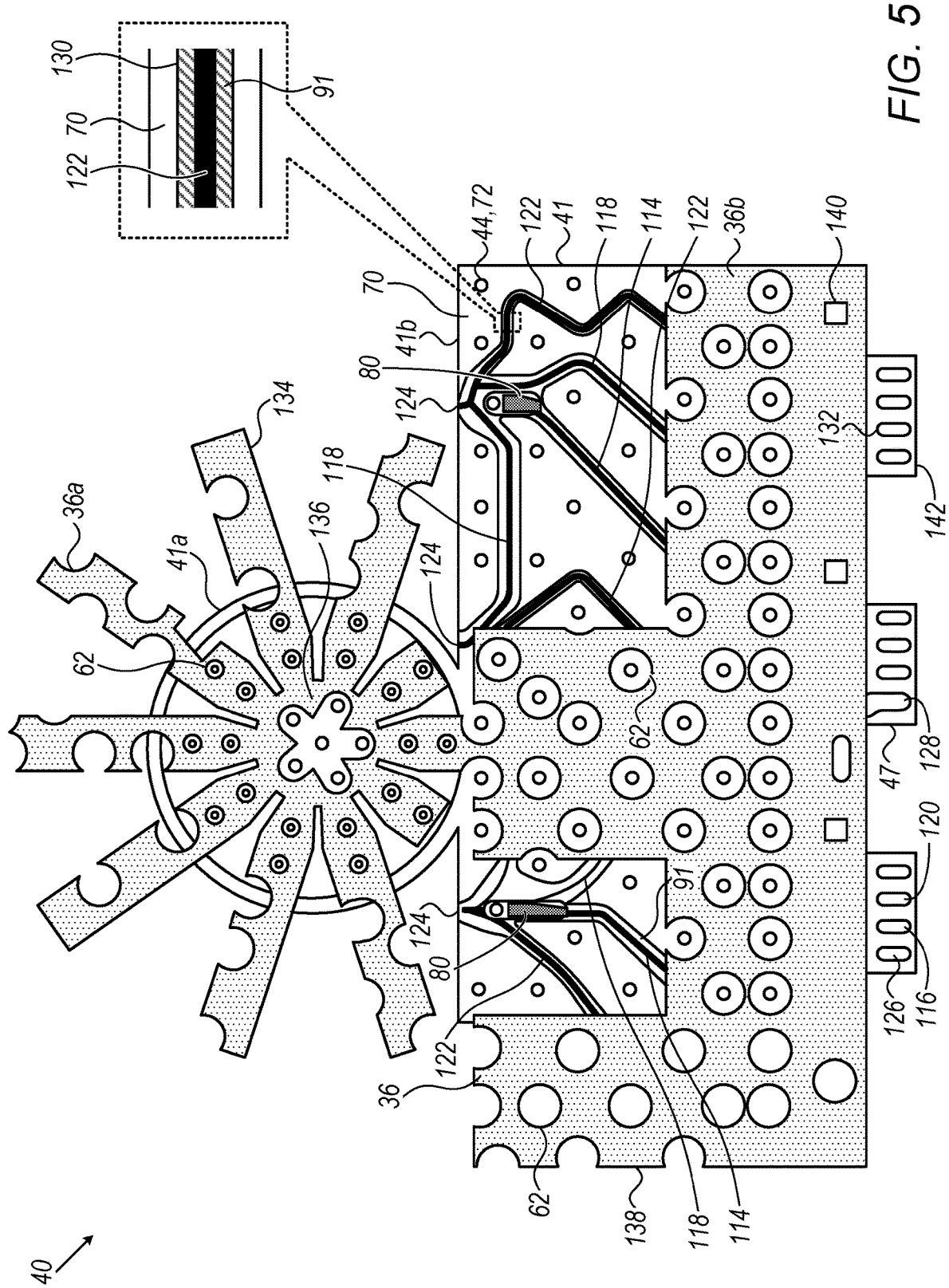
FIG. 5 is a schematic illustration of an ablation electrode prior to the deformation thereof, in accordance with some embodiments of the present invention.

Reference is now made to FIG. 4, which is a flow diagram for a method 82 of manufacturing electrode 40, in accordance with some embodiments of the present invention. Reference is additionally made to FIG. 5, which is a schematic illustration of electrode 40 prior to the deformation thereof, in accordance with some embodiments of the present invention. (FIG. 5 shows the interior of electrode 40, i.e., the various elements that are coupled to the inner surface of substrate 41.)

FIG. 4 assumes that at least the inner surface of the substrate is initially coated with a layer of copper. Hence, method 82 begins with an etching step 84, in which all of the copper is etched away from the inner surface, with the exception of copper traces 114, which are to be connected to the sensing electrodes on the exterior of the electrode. (Any copper on the outer surface is also etched away.) This etching may be performed, for example, by placing a mask over the portions of the copper that are designated for traces 114, and then chemically removing the exposed copper. Alternatively, if the inner surface of the substrate is initially exposed, copper traces 114 may be deposited onto the inner surface.

Subsequently, at a trace-depositing step 86, constantan traces 118, which are to be used for thermocouples, are deposited onto the inner surface of the substrate. Trace-depositing step 86 may be performed, for example, by physical vapor deposition (PVD), such as sputter deposition. For example, a mask may be placed over the entire inner surface, with the exception of those portions of the inner surface that are designated for constantan traces 118. Subsequently, a seed layer of a base metal, such as titanium-tungsten, may be sputtered onto the substrate. Finally, the constantan may be sputtered over the base metal.

Typically, to minimize the required wiring, the constantan traces terminate at a common constantan-trace soldering pad 120. In some embodiments, prior to the deposition of the constantan, a hole (or "stake via") is drilled through the substrate at the site of soldering pad 120. Subsequently, the deposited constantan fills the hole, and then forms soldering pad 120 above the hole. Alternatively, instead of drilling completely through the substrate, a depression may be drilled into the substrate, such that the deposited constantan fills the depression. In either case, soldering pad 120 is "staked" to the substrate by the constantan underneath the soldering pad. (To facilitate the filling of the hole or depression, a draft angle may be used to taper the hole or depression, as described immediately below for the narrower and wider channels.)

Next, at a drilling step 88, narrower channels and wider channels are drilled through the substrate, typically using laser drilling. (The wider channels, but not the narrower channels, may be seen in FIG. 5.) Typically, the channels are drilled from the inner surface of the substrate, using a draft angle such that the channels narrow as they approach the outer surface; this facilitates the collection of metal onto the walls of the channels during the subsequent sputtering process. In addition, blind vias 80 may be drilled (e.g., laser-drilled) through the substrate from the outer surface of the substrate at those portions of the outer surface that are designated for sensing electrodes, using copper traces 114 as stops. (In other words, portions of the substrate that are disposed over the copper traces may be removed, thus exposing the copper traces.) Typically, a draft angle is used for the blind vias, such that the blind vias narrow as they approach the inner surface of the substrate; this facilitates the collection of metal onto the walls of the blind vias.

(Typically, following drilling step 88, the substrate is treated with plasma to remove thermally damaged portions of the substrate. Typically, as a result of this treatment process, the channels are widened; hence, the size of each channel as drilled may be narrower than the desired final size of the channel.)

Next, at a first masking step 90, the copper and constantan traces, along with exclusion zones 91 (i.e., exposed portions of the inner surface of the substrate) that are designated for insulating these traces, are masked. (Portions of the constantan traces that are designated for the thermocouple junctions are not masked.) Additional exclusion zones designated for insulating the gold traces that will intersect the constantan traces (thus forming constantan-gold thermocouples) are also masked. Additionally, exclusion zones on the outer surface that are designated for insulating the sensing electrodes are masked.

Subsequently, at a depositing step 92, a thin layer of gold is deposited onto the inner and outer surfaces of the substrate and into the channels. Depositing step 92 may be performed, for example, by physical vapor deposition (PVD), such as sputter deposition. (Typically, a seed layer of a base metal, such as titanium-tungsten, is sputtered onto the substrate prior to the sputtering of the gold.) By virtue of the masks, the gold is not deposited onto the traces or exclusion zones.

The deposited gold includes an initializing layer for inner layer 70, outer layer 50, plating layer 52, and columns 48. The deposited gold further includes gold traces 122 that cover the constantan traces at thermocouple junctions 124. Each gold trace 122 terminates at a respective gold-trace soldering pad 126. The deposited gold further includes a respective copper-trace soldering pad 116 for each of the copper traces. In some embodiments, copper-trace soldering pads 116 and/or gold-trace soldering pads 126 are staked to the substrate, as described above for the constantan-trace soldering pad. The deposited gold further includes at least one gold soldering pad 128, which is connected to inner layer 70. Gold soldering pad 128 may also be staked to the substrate.

Following the deposition, the masks (along with any gold that was deposited onto the masks) are removed at a mask-removing step 93. Subsequently, at a second masking step 94, the traces, the inner-surface exclusion zones that surround the traces, and the entire outer surface of the substrate are masked.

Following second masking step 94, while the traces and outer surface remain masked, the substrate is plated in a plating bath of gold for a first time interval, at a first plating step 98. The plating of the substrate causes any gaps in the gold to be filled, and further increases the thickness of the gold, such that, for example, inner layer 70 reaches a thickness of between 5 and 40 microns, while the diameter of the wider channels is reduced to between 30 and 200 microns. Additionally, the narrower channels may become completely filled.

Typically, the plating of the substrate is electrochemical, whereby the flow of electric current through the gold that already coats the substrate causes this gold to attract gold ions in the plating bath. The amplitude and duration of the current may be controlled such that the gold reaches the desired thickness.

Following first plating step 98, the inner and outer surfaces of the substrate, with the exception of the aforementioned exclusion zones designated to insulate the sensing electrodes, are unmasked, at an unmasking step 100. Next, at a coverlay-applying step 101, at least one coverlay 130 is applied over the traces and inner-surface exclusion zones. (In some embodiments, as illustrated in the inset portion of FIG. 5, coverlay 130 is transparent or nearly transparent.)

Typically, the proximal portion of coverlay 130 that covers tabs 47 is shaped to define windows 132 that expose the soldering pads, such that the soldering pads may be thickened during the subsequent plating process. (An additional cover 142, having windows that are aligned with windows 132, may cover the proximal portion of the coverlay.) Typically, the soldering pads are not completely exposed, but rather, are held "captive" by coverlay 130, in that one or more edges of each soldering pad are covered by the rims of windows 132. Coverlay 130 thus helps hold the soldering pads to substrate 41 during the subsequent soldering process.

Subsequently, at a second plating step 102, the substrate is plated in the plating bath for a second time interval, such that any gaps in outer layer 50 are filled, while the inner, outer, and plating layers are thickened. For example, the second plating may increase the thickness of the inner layer to between 10 and 50 microns, while reducing the diameter of the wider channels to between 15 and 150 microns. Typically, the final thickness of the inner layer is the same as the thickness of the coverlay, such as to attain a smooth interior surface. (To avoid any confusion, the term "interior surface" is used herein to refer to the surface that is formed by the coverlay and the inner gold layer, whereas the term "inner surface" is used to refer to the underlying surface of the substrate.) Additionally, in the event that the narrower channels were not completely filled during first plating step 98, these channels are completely filled during second plating step 102. As in the case of first plating step 98, the amplitude and duration of the electric current in the plating bath may be controlled such that the desired thicknesses are attained.

(In some embodiments, the outer surface is masked prior to depositing step 92, such that no gold is deposited onto the outer surface during depositing step 92. In such embodiments, following unmasking step 100 and prior to second plating step 102, a thin layer of gold is deposited onto the outer surface.)

In some embodiments, as assumed in FIGS. 4-5, supporting structure 36 comprises a supporting sheet that is deformed, following the bonding of the PCB (i.e., the substrate together with the various elements disposed thereon) to the supporting sheet, into a suitable three-dimensional shape. In such embodiments, subsequently to second plating step 102 at an aperture-drilling step 104, apertures 62 may be drilled through the supporting sheet. (Alternatively to drilling, any other suitable technique, such as chemical etching, may be used to form the apertures.) Subsequently, depressions and/or protrusions may be formed in the surface of the sheet. The depressions and protrusions, along with the steps by which they may be formed (comprising a third masking step 105, a chemical etching step 107, and a sheet-removing step 109), are described below with reference to FIGS. 6A-B.

Following second plating step 102 and, optionally, the drilling of apertures and/or the formation of depressions and/or protrusions in the supporting sheet, a bonding step 106 is performed. At bonding step 106, an adhesive is applied between the outer surface of the supporting structure and the interior surface of the PCB formed by coverlay 130 and inner layer 70, such that the adhesive bonds these two surfaces to one another. Typically, the supporting structure is bonded to the interior surface such that apertures 62 are aligned with irrigation holes 72. Typically, the area of the apertures is greater than that of the irrigation holes, such as to compensate for any small misalignments during the bonding. In some embodiments, as described below with reference to FIG. 8, the apertures are much larger than the irrigation holes, so as to additionally expose a large portion of the interior surface to the irrigating fluid.

Subsequently to or concurrently with the bonding, at a deforming step 108, electrode 40 is deformed into the desired shape. For example, assuming the supporting structure initially comprises a flat supporting sheet as shown in FIG. 5, the electrode may be inserted, following bonding step 106, into a forming jig that shapes the electrode around a suitable mandrel. Following the insertion of the electrode into the jig, the jig is placed inside an oven. Subsequently, the oven heats the electrode to a suitable temperature, while pressure is applied to the electrode. The combination of heat and pressure causes the electrode to bond to itself in the desired shape.

In general, the substrate and supporting sheet may be deformed into any desired shape. Typically, however, during deforming step 108, the substrate and supporting sheet are shaped to define an interior lumen that is at least partly enclosed by the inner surface of the sheet. For example, as described above with reference to FIGS. 2A-B, the substrate and supporting sheet may be shaped to define a thimble.

In some embodiments, to facilitate the manufacture of a thimble-shaped electrode, substrate 41 comprises two portions that are continuous with one another: a distal, circular portion 41a, and a proximal, rectangular portion 41b. Similarly, the supporting sheet comprises two portions that are continuous with one another: a distal supporting portion 36a, which may comprise a plurality of spokes 134 that radiate from a central hub 136, and a proximal supporting portion 36b. During bonding step 106, distal supporting portion 36a is bonded to the interior surface of circular portion 41a, and the adhesive is applied to the outer surface of distal supporting portion 36a, e.g., to the outer surface of each spoke 134. In addition, proximal supporting portion 36b is bonded to the interior surface of rectangular portion 41b, leaving some distal portions of this interior surface exposed. The adhesive is applied to the outer surface of an overhanging tab 138 of proximal supporting portion 36b, which hangs over the side of rectangular portion 41b. (Proximal supporting portion 36b may also hang over the proximal end of rectangular portion 41b.)

Subsequently, during deforming step 108, distal supporting portion 36a and circular portion 41a are folded over the top of the mandrel, while proximal supporting portion 36b and rectangular portion 41b are rolled around the mandrel. To maintain this configuration, the outer surface of distal supporting portion 36a (e.g., the outer surface of each spoke 134) is bonded to the exposed distal portions of the interior surface of rectangular portion 41b, and the outer surface of tab 138 is bonded to the opposite end of proximal supporting portion 36b. (Additionally, the inner surface of at least one of the spokes may bond to tab 138.) Thus, distal supporting portion 36a and circular portion 41a are formed into dome-shaped portion 40a (FIG. 2A), while proximal supporting portion 36b and rectangular portion 41b are formed into cylindrical portion 40b.

Subsequently, at a soldering step 110, wires are soldered onto the soldering pads. In particular, the wire that delivers RF current from generator 27 (FIG. 1) is soldered onto gold soldering pad 128, while other wires, which deliver signals to processor 23, are soldered to the other soldering pads.

Finally, at a coupling step 112, the electrode is coupled to the probe. For example, proximal supporting portion 36b may be bonded to base 58 of the flow diverter (FIG. 2B). Alternatively or additionally, as described above with reference to FIG. 2B, protrusions belonging to base 58 may snap into complementary holes 140 in proximal supporting portion 36b. Subsequently, the flow diverter may be coupled to the fluid-delivery tube belonging to the probe. (Alternatively, the flow diverter may be coupled to the fluid-delivery tube before the electrode is coupled to the flow diverter.)

Alternatively or additionally to the traces described above, any other suitable electric or electronic components may be deposited onto the inner surface of the substrate. Such components may include thermistors for measuring the temperature of the tissue, pressure sensors for measuring the pressure applied to the distal end of the probe, and/or electromagnetic sensors for navigating the probe. These components (along with suitable surrounding exclusion zones) may be masked or covered whenever such masking or covering is required, as described above for the traces.

It is noted that the scope of the present disclosure includes any suitable modification to method 82 with respect to the order of the steps that are performed and/or with respect to the various materials that are used, as will be apparent to any person of skill in the art. For example, any suitable electrically-conducting metal may be used in lieu of copper, gold, or constantan.

Heat Transfer

To facilitate the transfer of heat to the irrigating fluid as the fluid flows through the electrode, various techniques may be used to increase the surface area of the inner surface of the supporting structure, to increase the turbulence of the flow of the fluid, to increase the transfer of heat from the PCB to the supporting structure, to increase the area over which the fluid may directly contact the interior surface of the PCB, and/or to increase the cross-sectional area of the thermal vias.

In this regard, reference is first made to FIG. 6A, which is a schematic illustration of a method for forming depressions in a surface of supporting structure 36, in accordance with some embodiments of the present invention. Reference is also made to FIG. 6B, which is a schematic illustration of a method for forming protrusions on another surface of supporting structure 36, in accordance with some embodiments of the present invention.

In some embodiments, as shown in FIGS. 6A-B, multiple depressions 144 are formed in the outer surface 146 of supporting structure 36 (i.e., the surface of the structure designated for bonding to the PCB), and/or multiple protrusions 148 are formed on the inner surface 150 of the structure. Typically, the formation of depressions 144 and/or protrusions 148 is performed for embodiments in which the supporting structure initially a flat sheet, as shown in FIG. 5. Hence, the description of FIGS. 6A-B below generally uses the term "sheet" when referring to the supporting structure.

In some embodiments, to form depressions 144, an outer mask 152, which is shaped to define a plurality of mask apertures 154, is coupled to outer surface 146. Subsequently, the sheet is placed into a chemical etching bath and is left in the bath for a predetermined duration of time, such that portions of outer surface 146 exposed by mask apertures 154 are etched away. Similarly, to form protrusions 148, multiple inner masks 156 are coupled to inner surface 150, and the sheet is then placed into a chemical etching bath and is left in the bath for a predetermined duration of time, such that the portions of the inner surface disposed between masks 156 are etched away.

Typically, both depressions 144 and protrusions 148 are formed. In some embodiments, the depressions and protrusions are formed simultaneously. (In such embodiments, the height of the protrusions is approximately equal to the depth of the depressions.) For example, returning to FIG. 4, at a third masking step 105, outer mask 152 may be coupled to the outer surface of the sheet, and inner masks 156 may be coupled to the inner surface of the sheet. Subsequently, at a chemical etching step 107, the sheet may be placed into the bath, such that both the depressions and protrusions are formed. Following the formation of the depressions and protrusions, the sheet is removed from the bath, at a sheet-removing step 109.

In other embodiments, the depressions and protrusions are formed at separate times. For example, during a first chemical etching step, the outer surface of the sheet may be masked by outer mask 152 while the inner surface of the sheet is completely masked, such that the depressions, but not the protrusions, are formed. Subsequently, during a second chemical etching step, the inner surface of the sheet may be masked by the inner masks while the outer surface of the sheet is completely masked, such that the protrusions are formed. Advantageously, this technique facilitates a protrusion height that is different from the depression depth, in that the respective durations of the two chemical etching steps may be made different from one another.

In some embodiments, each mask aperture 154 is circular, such that each depression 144 has a circular perimeter. In such embodiments, the diameter L2 of each mask aperture may be between 0.01 and 0.2 mm. Alternatively, some or all of the mask apertures may have any other suitable shape.

Mask apertures 154 (and hence, depressions 144) may be arranged in a grid pattern, or in any other suitable arrangement. For example, as shown in FIG. 6A, a plurality of circular mask apertures may be arranged in a close-packed pattern, with a distance L3 of between 0.05 and 0.5 mm between the respective centers of neighboring mask apertures. In some embodiments, L3 is approximately twice L2.

In some embodiments, each inner mask 156 is rectangular, such that (the inner surface of) each protrusion 148 has a rectangular perimeter. For example, each inner mask may be square-shaped, having a length L0 of between 0.01 and 0.2 mm. Alternatively, some or all of the inner masks may have any other suitable shape. For example, each inner mask may be star-shaped, such that the perimeter of (the inner surface of) each of the protrusions is star-shaped. Examples of such shapes—which provide a relatively large amount of surface area for contact with the irrigating fluid, and a large number of edges for generating turbulent flow—include those of N-pointed stars, where N is three or more.

Inner masks 156 (and hence, protrusions 148) may be arranged in any suitable arrangement, such as a grid pattern. For example, a plurality of square inner masks may be arranged in a grid, with a distance L1 of between 0.05 and 0.5 mm separating between neighboring squares. In some embodiments, the distance between neighboring squares is approximately equal to the length of each square, i.e., L1 is approximately equal to L0.

Figure 7:
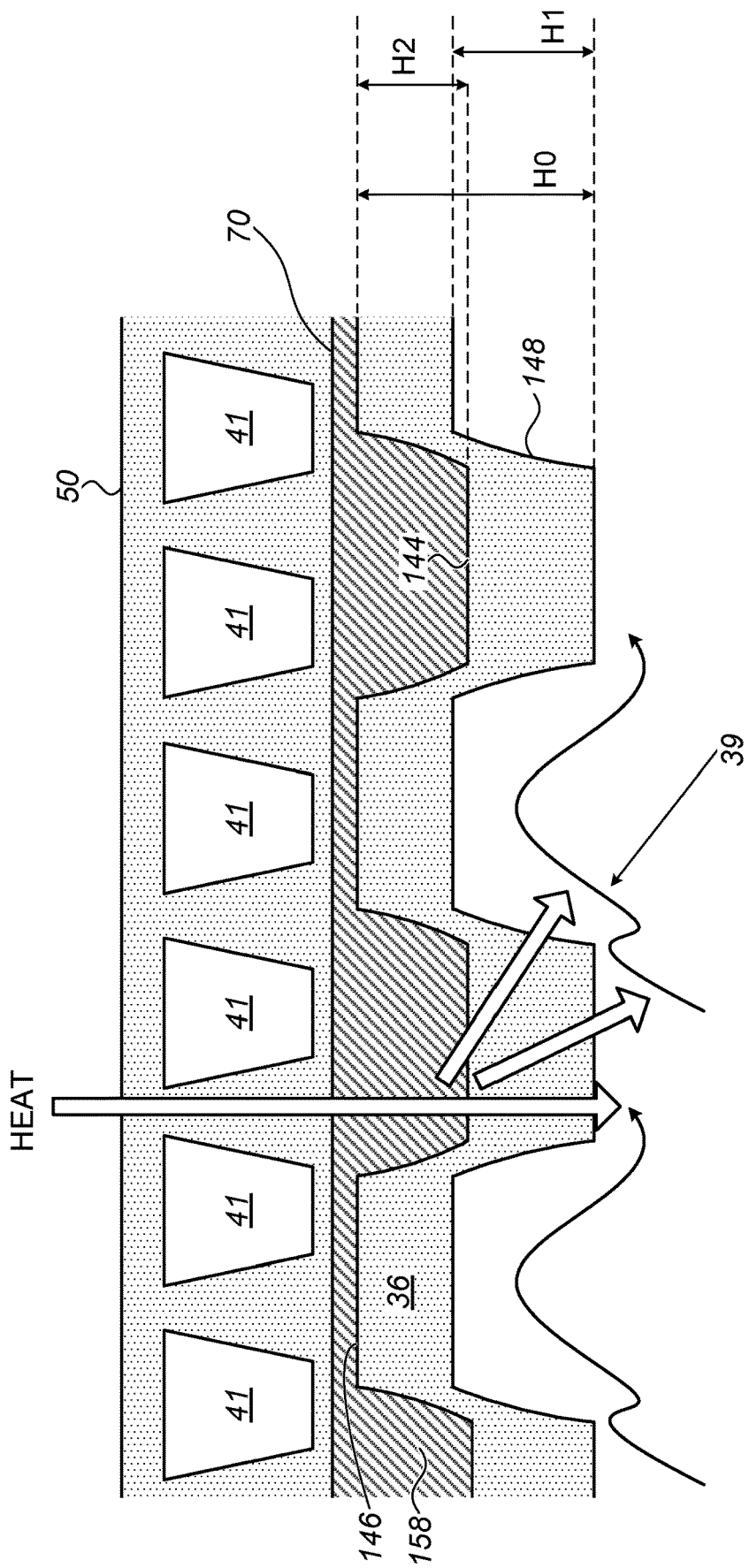
FIG. 7 schematically illustrates the transfer of heat to the interior of an ablation electrode, in accordance with some embodiments of the present invention.

Typically, the area of each aperture 154 is smaller than the area of each inner mask 156, and the inner masks are aligned with the outer masks such that the entire perimeter of each aperture is opposite a respective inner mask. (This reduces the risk of a thru-hole being accidentally formed during the chemical etching process.) As a result of this sizing and alignment, each of the depressions is entirely opposite a protrusion (as illustrated in FIG. 7, which is described below).

Alternatively to chemical etching, other techniques, such as laser etching, may be used to form protrusions 148 and/or depressions 144.

In some embodiments, the substrate and supporting sheet are shaped to define a ring or an arc. In some such embodiments, a plurality of such ring-shaped and/or arc-shaped electrodes are coupled to each other at the distal end of the probe, so as to define a ball. By virtue of spaces between the rings and/or arcs, blood may flow through the ball during the ablation procedure. Hence, the heat generated from the ablation may be transferred from protrusions 148 directly to the blood of the subject.

In general, any suitable masking technique may be used at each of the steps in which a mask is required. Examples of suitable masks include liquid and film photoresists.

Reference is now made to FIG. 7, which schematically illustrates the transfer of heat to the interior of electrode 40, in accordance with some embodiments of the present invention.

As described above with reference to FIG. 4, an adhesive 158 bonds supporting structure 36 to the interior surface of the PCB. Advantageously, in some embodiments, adhesive 158 fills depressions 144, thus improving the adhesion of the supporting structure to the PCB, while also reducing the amount of adhesive that interposes between the undepressed portion of outer surface 146 and the PCB. In other words, by virtue of the adhesive collecting in the depressions, outer surface 146 may contact, or nearly contact, the interior surface of the PCB. As a result, more heat may be transferred to the supporting structure.

As further described above, during and/or following the application of the ablation currents, irrigating fluid 39 is made to flow through the electrode, such that, in some embodiments, the irrigating fluid flows over the surface of protrusions 148. By virtue of the large surface area provided by the protrusions, and/or by virtue of the turbulent flow caused by the protrusions, a large amount of heat is transferred from the protrusions to fluid 39. (As described above with reference to FIGS. 6A-B, in some embodiments, the subject's blood, rather than fluid 39, flows over the surface of the protrusions, such that the heat is transferred from the protrusions directly to the blood.)

In some embodiments, the height H1 of each protrusion, and/or the depth H2 of each depression, is between 5% and 60% of the thickness H0 of the supporting structure. (As described above with reference to FIGS. 6A-B, by forming the depressions and protrusions in two separate chemical etching steps, the depth of the depressions may be made different from the height of the protrusions.) For example, if H0 is between 0.025 and 0.2 mm, each of H1 and H2 may be between 0.00125 and 0.12 mm.

In some embodiments, alternatively or additionally to forming depressions in the supporting structure, depressions are formed in inner layer 70. Each depression (or "dimple") may be formed, for example, by using a laser to melt a small portion of the metal and to displace the molten metal radially outward. Upon solidifying, the molten metal forms a rim that surrounds the depression.

Typically, the depressions are circular and are arranged in a close-packed pattern, as shown for depressions 144 in FIG. 6A. Those depressions that are opposite the supporting structure may facilitate the bonding of the PCB to the supporting structure (as described above for depressions 144), while those depressions that are exposed to the irrigating fluid may facilitate greater heat transfer to the irrigating fluid by increasing the turbulence of the flow.

Figure 8:
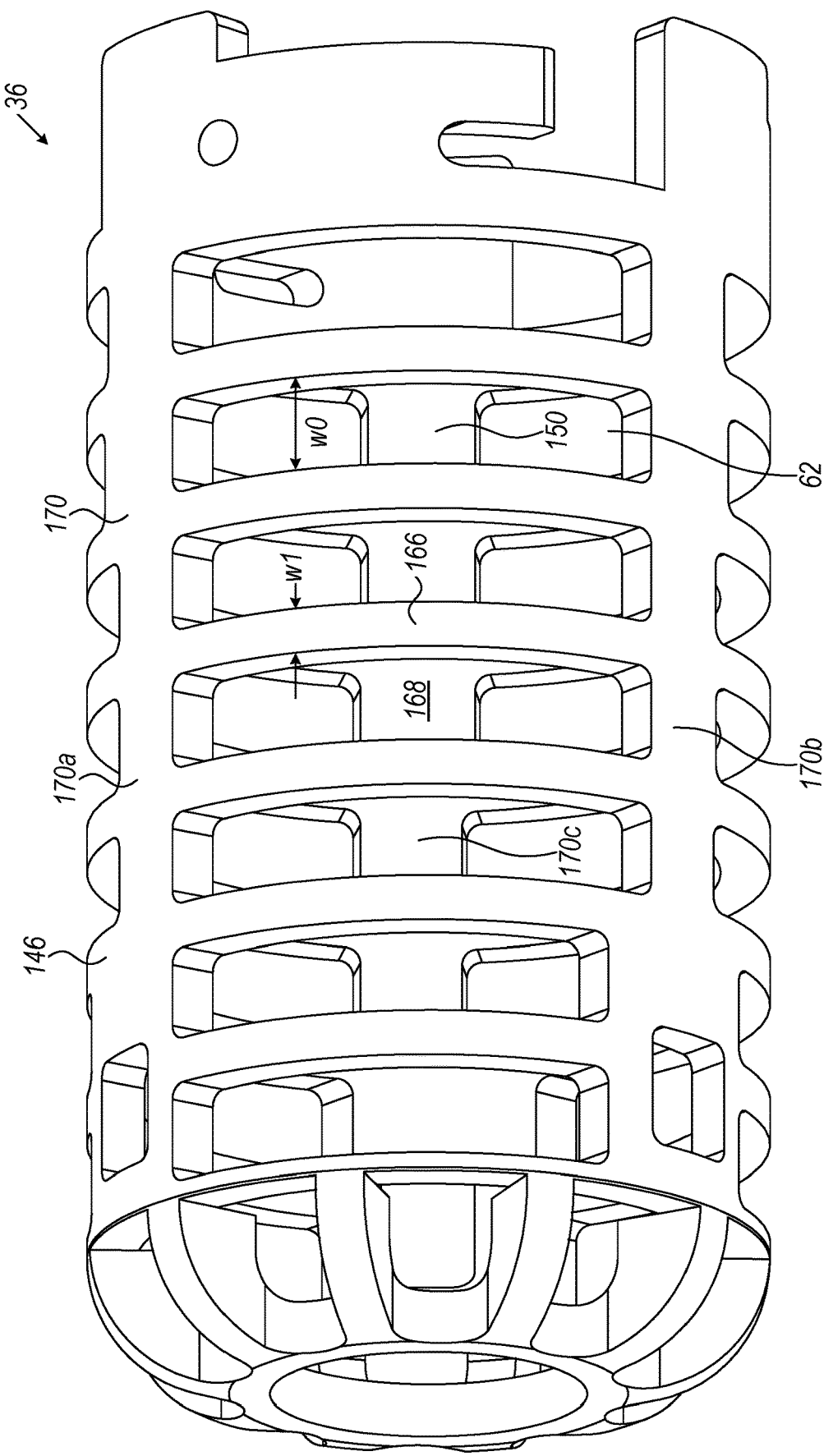
FIG. 8 is a schematic illustration of a supporting structure, in accordance with some embodiments of the present invention.

Reference is now made to FIG. 8, which is a schematic illustration of supporting structure 36, in accordance with some embodiments of the present invention.

In some embodiments, supporting structure 36 comprises a plurality of ribs 166 surrounding an interior lumen 168 through which, as described above with reference to FIG. 2B, the irrigating fluid flows. In such embodiments, apertures 62, each of which separates a pair of successive ribs 166 from one other, are typically relatively wide. For example, the width w0 of each of the apertures may be wider, e.g., 50%-300% wider, such as 80%-150% wider, than the width w1 of each of the ribs. In addition to exposing the irrigation holes in the PCB, the apertures expose a relatively large portion of the interior surface of the PCB. Thus, heat may be transferred directly from the PCB to the irrigating fluid. The transfer of heat may be increased even further by the provision of depressions in the interior surface of the PCB, as described above with reference to FIG. 7.

(Another advantage of such embodiments, relative to embodiments in which the supporting structure is made from a flat sheet of metal, is that the ribs may enhance the structural integrity of the supporting structure.)

Typically, ribs 166 are circumferentially-oriented, the end of each rib being joined to or continuous with a support column 170 running along the length of the structure. Typically, the ribs are arranged in multiple rows. For example, as shown in FIG. 8, the supporting structure may comprise three rows of ribs: a first row disposed between a first support column 170a and a second support column 170b, a second row between second support column 170b and a third support column 170c, and a third row between third support column 170c and the first support column.

In some embodiments, supporting structure 36 comprises a molded polymer such as PEEK, e.g., glass-filled PEEK. In such embodiments, outer surface 146 is typically rough as a result of the molding process. Alternatively or additionally, the outer surface may be roughened following the molding process; for example, the outer surface may be plasma etched so as to expose some of the glass that fills the PEEK. The roughness of the outer surface may facilitate bonding and heat transfer, as described above for depressions 144 (FIG. 6A).

In other embodiments, the supporting structure comprises machined metal.

To shape the electrode, bonding step 106 and deforming step 108 (FIG. 4) may be performed concurrently. In other words, following the application of the adhesive to the supporting structure, the PCB may be wrapped around the supporting structure. To facilitate the bonding, heat and/or pressure may be applied to the electrode during and/or following the wrapping of the PCB.

Figure 9:
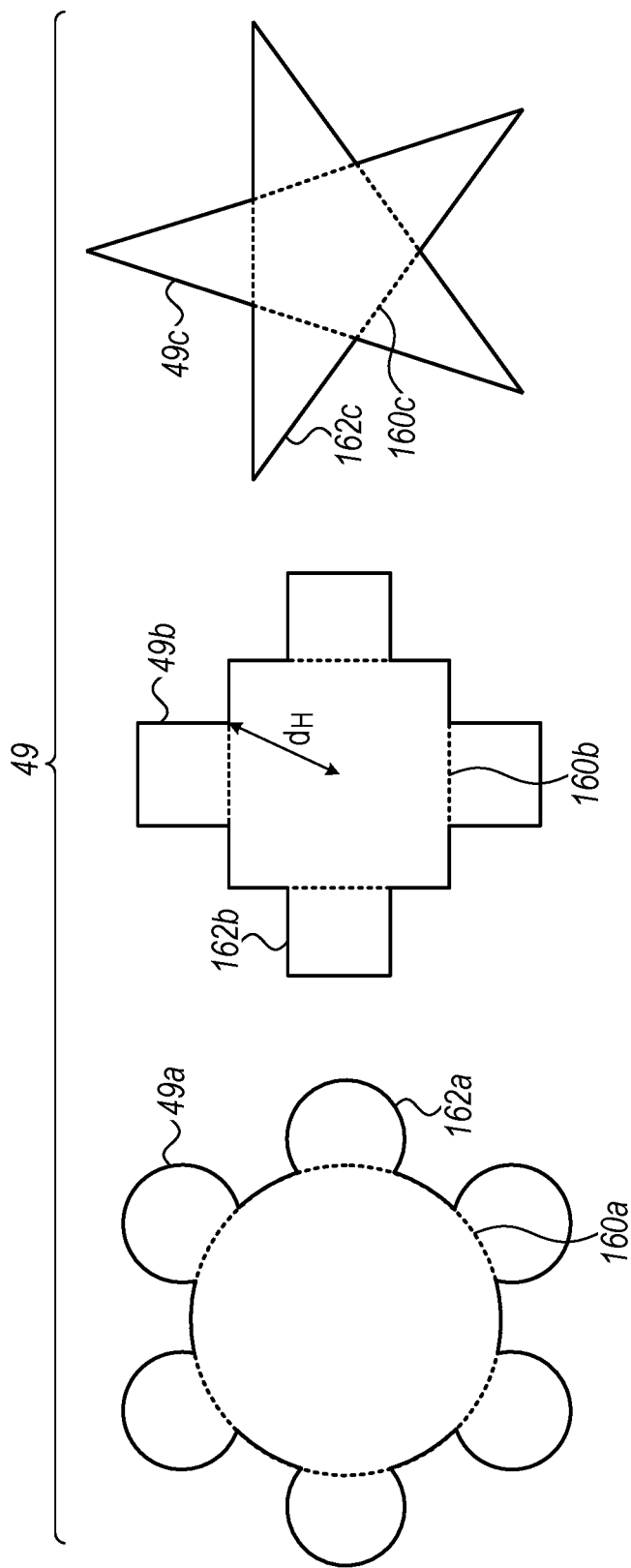
FIG. 9 is a schematic illustration of various types of concave channels, in accordance with some embodiments of the present invention.

Reference is now made to FIG. 9, which is a schematic illustration of various types of concave channels 49, in accordance with some embodiments of the present invention.

As described above with reference to FIGS. 2A and 3B, substrate 41 is shaped to define a plurality of concave channels 49, which are filled with columns of metal. In general, the scope of the present invention includes any suitable concave shape for channels 49 (and hence, for the columns of metal that fill the channels). By way of example, FIG. 9 shows a concave channel 49a having a first shape, another concave channel 49b having a second shape, and yet another concave channel 49c having a third shape.

Concave channel 49a comprises a circular central channel-portion 160a and one or more (e.g., 2-8) peripheral channel-portions 162a opening into central channel-portion 160a. Peripheral channel-portions 162a have arced perimeters, such that the peripheral channel-portions are shaped as part-circles.

Concave channel 49b and concave channel 49c each comprise a polygonal central channel-portion and one or more peripheral channel-portions opening into the central channel-portion. In concave channel 49b, the central channel-portion 160b and the peripheral channel-portions 162b are rectangular. For example, central channel-portion 160b and/or peripheral channel-portions 162b may be square. Concave channel 49c has a star shape, in that the channel includes a central channel-portion 160c shaped as an N-sided polygon, N being three or more, along with N triangular peripheral channel-portions 162c, each opening into central channel-portion 160c at a different respective edge of the polygon.

Advantageously, as described above in the Overview, the concave channels provide a relatively long perimeter onto which the metal may nucleate during the plating process, and also decrease the distance from the perimeter to the interior of the channel. Hence, the channel may provide a large cross-sectional surface area and yet nonetheless fill relatively quickly during the plating process.

By way of example, to demonstrate this advantage, it will be assumed that in channel 49b, each peripheral channel-portion is a square having a length of one arbitrary unit (AU) and the central channel-portion is a square of length 3 AU. Assuming these dimensions, the transverse cross-sectional area of the channel is 13 $AU^2$ and the perimeter of the channel is 20 AU. In contrast, though a channel shaped as a (convex) square of length $\sqrt{13}$ AU could provide the same cross-sectional area (and hence, the same amount of heat transfer), the perimeter of this channel would be only $4\sqrt{13}$ (approximately 14.4) AU. Moreover, whereas the Hausdorff distance $d_H$ from the interior of channel 49b (assuming the dimensions above) to the perimeter of the channel is only 1.58 AU, the Hausdorff distance from the interior to the perimeter of the convex channel would be 1.8 AU.

Figure 10:
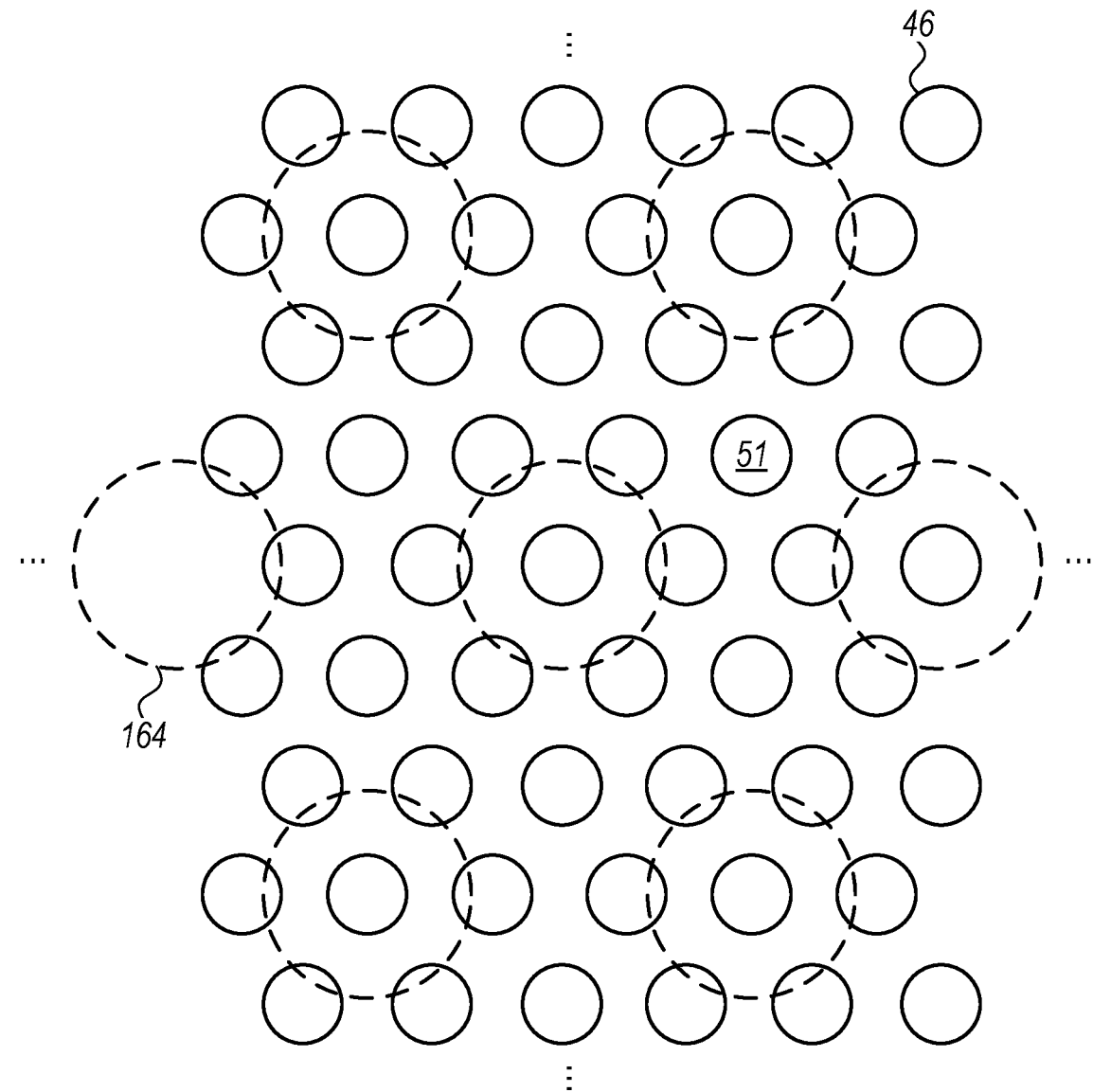
FIG. 10 is a schematic illustration of an arrangement of channels, in accordance with some embodiments of the present invention.

Reference is now also made to FIG. 10, which is a schematic illustration of an arrangement of channels 46, in accordance with some embodiments of the present invention.

Typically, concave channel 49a includes exactly six peripheral channel-portions opening into the central channel-portion. In such embodiments, to form concave channel 49a, drilling step 88 (FIG. 4) may be performed in two stages. In particular, during a first pass of the drill, a close-packed pattern of circular channels 46 may be drilled through the substrate, as shown in FIG. 10. (In this close-packed pattern, the distance between the respective centers of neighboring channels may be between 20 and 60 μm, for example.) Next, during a second pass of the drill, some of the circular channels may be expanded such that each of the expanded circular channels opens into the surrounding six channels, thus forming a concave channel 49a. An advantage of forming the channels in this manner is that only circular cuts are required.

For example, as indicated by the dashed expansion indicators 164 in FIG. 10, every third channel in both the vertical and horizontal directions may be expanded. Following the expansion of every third channel, channels 46 are arranged such that each of at least some of the convex channels 51 is surrounded by a respective three of the concave channels.

Alternatively, the arrangement of channels illustrated in FIG. 10 may be obtained during a single pass of the drill, by tracing the respective perimeters of both the circular channels and the concave channels.

In some embodiments, at least one of the convex thermal vias has a length that is at least twice the width of the via. (Such a via may be shaped, for example, as an ellipse or a rectangle.) Advantageously, such vias may provide a relatively large perimeter while also providing a relatively small distance from the perimeter to the interior of the via.

In general, the embodiments described herein may be combined with any of the embodiments described in US Patent Application Publication 2018/0110562, issued as U.S. Pat. No. 10,898,262 on Jan. 26, 2021, or US Patent Application Publication 2019/0117296, issued as U.S. Pat. No. 10,874,456 on Dec. 29, 2020, whose respective disclosures are incorporated herein by reference.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) a flexible electrically-insulating substrate, comprising an inner surface and an outer surface, and shaped to define multiple channels passing between the inner surface and the outer surface, a first set of the multiple channels being concave channels, each of the concave channels comprising:

(i) a circular central channel-portion, and
(ii) one or more peripheral channel-portions opening into the central channel-portion, the one or more peripheral channel-portions comprising at least three peripheral channel-portions;

(b) an outer layer of an electrically-conducting metal covering at least part of the outer surface;

(c) an inner layer of the electrically-conducting metal covering at least part of the inner surface; and (d) respective columns of the electrically-conducting metal that fill the multiple channels to connect the outer layer to the inner layer.

2. The apparatus according to claim 1, the at least three peripheral channel-portions consisting of six peripheral channel-portions.

3. The apparatus according to claim 2, the concave channels including at least three concave channels, a second set of the multiple channels comprising circular channels arranged such that one of the circular channels is surrounded by the at least three concave channels.

4. The apparatus according to claim 1, the central channel-portion of each of the concave channels being polygonal.

5. The apparatus according to claim 4, the central channel-portion and the peripheral channel-portions being rectangular.

6. The apparatus according to claim 4, each of the concave channels having a star shape.

7. The apparatus according to claim 1, a total area of respective outer openings of the multiple channels being at least 30% of an area of the outer surface.

8. The apparatus according to claim 1, the electrically-conducting metal comprising gold.

9. The apparatus according to claim 1, further comprising:
(a) a probe configured for insertion into a body of a subject; and
(b) a supporting structure bonded to the inner layer and coupled to a distal end of the probe.

10. The apparatus according to claim 9, the supporting structure comprising a plurality of ribs surrounding a lumen, successive ones of the plurality of ribs being separated from one another by an aperture that is wider than each of the plurality of ribs.

11. The apparatus according to claim 1, a surface of the inner layer being shaped to define a plurality of depressions.

12. The apparatus according to claim 11, the plurality of depressions being circular and being arranged in a close-packed pattern.

13. The apparatus according to claim 1, an average transverse cross-sectional area of each of the concave channels being between 345 and 15,700 $\mu m^2$.

14. The apparatus according to claim 1, the central channel-portion of each of the concave channels being circular.

15. The apparatus according to claim 14, each of the one or more peripheral channel-portions having an arced perimeter.

16. An apparatus, comprising:
(a) a flexible electrically-insulating substrate, comprising an inner surface and an outer surface, and shaped to define multiple channels passing between the inner surface and the outer surface, at least some of the multiple channels being concave channels, each of the concave channels comprising:
(i) a polygonal central channel-portion, and
(ii) one or more peripheral channel-portions opening into the central channel-portion;
(b) an outer layer of an electrically-conducting metal covering at least part of the outer surface;
(c) an inner layer of the electrically-conducting metal covering at least part of the inner surface; and
(d) respective columns of the electrically-conducting metal that fill the multiple channels to connect the outer layer to the inner layer.

17. The apparatus according to claim 16, the central channel-portion and the one or more peripheral channel-portions being rectangular.

18. The apparatus according to claim 16, each of the concave channels having a star shape.

* * * * *